US008754032B2

(12) United States Patent
Abe et al.

(10) Patent No.: US 8,754,032 B2
(45) Date of Patent: Jun. 17, 2014

(54) CONCOMITANT PHARMACEUTICAL AGENTS AND USE THEREOF

(75) Inventors: Yuji Abe, Osaka (JP); Jun Anabuki, Osaka (JP); Fumihiko Akahoshi, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 881 days.

(21) Appl. No.: 11/916,356

(22) PCT Filed: Jun. 2, 2006

(86) PCT No.: PCT/JP2006/311073
§ 371 (c)(1),
(2), (4) Date: Mar. 4, 2008

(87) PCT Pub. No.: WO2006/129785
PCT Pub. Date: Dec. 7, 2006

(65) Prior Publication Data
US 2009/0082256 A1    Mar. 26, 2009

(30) Foreign Application Priority Data

Jun. 3, 2005   (JP) ................................ 2005-164213

(51) Int. Cl.
*A61K 31/133* (2006.01)
*A61K 31/155* (2006.01)

(52) U.S. Cl.
USPC ..................................... 514/1.1; 514/254.02

(58) Field of Classification Search
None
See application file for complete search history.

(56) References Cited

U.S. PATENT DOCUMENTS

| | | | |
|---|---|---|---|
| 6,710,040 B1 * | 3/2004 | Hulin et al. | 514/210.17 |
| 7,060,722 B2 * | 6/2006 | Kitajima et al. | 514/422 |
| 2003/0139434 A1 * | 7/2003 | Balkan et al. | 514/275 |
| 2003/0166578 A1 | 9/2003 | Arch et al. | |
| 2004/0106655 A1 | 6/2004 | Kitajima et al. | |
| 2004/0259883 A1 | 12/2004 | Sakashita et al. | |
| 2005/0245538 A1 * | 11/2005 | Kitajima et al. | 514/254.02 |

FOREIGN PATENT DOCUMENTS

| | | | |
|---|---|---|---|
| JP | WO 02/14271 | * | 2/2002 |
| JP | 2003-520226 A | | 7/2003 |
| JP | 2003-535898 A | | 12/2003 |
| WO | WO 02/14271 A1 | | 2/2002 |
| WO | WO 03/024942 A1 | | 3/2003 |

OTHER PUBLICATIONS

Ahren et al., *Diabetes Care*, 27(12): 2874-2880 (Dec. 2004).
Drucker, *Expert. Opin. Investig. Drugs*, 12(1): 87-100 (2003).

* cited by examiner

*Primary Examiner* — Karlheinz R Skowronek
*Assistant Examiner* — Roy Teller
(74) *Attorney, Agent, or Firm* — Leydig, Voit & Mayer, Ltd.

(57) ABSTRACT

A concomitant agent to be used simultaneously or separately, comprising a combination of (a) 3-{(2S,4S)-4-[4-(3-methyl-1-phenyl-1H-pyrazol-5-yl)piperazin-1-yl]pyrrolidin-2-ylcarbonyl}thiazolidine, a salt of the compound with an organic or inorganic and mono- or di-basic acid or a solvate thereof, and
(b) at least one kind of active ingredient selected from the group consisting of an active ingredient of a pharmaceutical agent selected from (i) an antidiabetic drug, (ii) a lipid lowering drug, (iii) an antihypertensive drug, (iv) a therapeutic drug for diabetic complications, (v) an antiobesity drug, (vi) an antiplatelet drug and (vii) an anticoagulant, a pharmaceutically acceptable salt thereof and a solvate thereof.

7 Claims, 2 Drawing Sheets

CONCOMITANT PHARMACEUTICAL AGENTS AND USE THEREOF

TECHNICAL FIELD

The present invention relates to a concomitant agent to be used simultaneously or separately, which comprises a combination of (a) 3-{(2S,4S)-4-[4-(3-methyl-1-phenyl-1H-pyrazol-5-yl)piperazin-1-yl]pyrrolidin-2-ylcarbonyl}thiazolidine, a salt of the compound with an organic or inorganic mono- or di-basic acid or a solvate thereof, and (b) at least one kind of active ingredient selected from the group consisting of the active ingredient of a pharmaceutical agent selected from (i) an antidiabetic drug, (ii) a lipid lowering drug, (iii) an antihypertensive drug, (iv) a therapeutic drug for diabetic complications, (v) an antiobesity drug, (vi) an antiplatelet drug and (vii) an anticoagulant, a pharmaceutically acceptable salt thereof and a solvate thereof.

BACKGROUND ART

Diabetes refers to a condition with abnormally elevated glucose concentration in blood (plasma glucose level), and is one of the important risk factors of arteriosclerotic diseases such as ischemic cardiac diseases and the like, in addition to diabetic microangiopathy.

Therefore, it is required to improve life style as well as control the plasma glucose level to an appropriate level by taking an antidiabetic drug.

At present, various antidiabetic drugs have been marketed and used in clinical situations. However, no single pharmaceutical agent is capable of sufficiently improving the complicated pathology of diabetes, and plural pharmaceutical agents are used in combination for diabetes treatment.

A representative concomitant drug for diabetes treatment is a sulfonylurea (hereinafter sometimes to be referred to as SU) agent. However, since SU agents have a risk of causing hypoglycemia, a particular attention is required when using plural pharmaceutical agents in combination. In addition, a long-term use of SU agent is feared to cause exhaustion of β-cell.

In recent years, a highly increased risk of arteriosclerotic diseases due to duplicative development of plural risk factors including abnormal glucose metabolism, abnormal lipid metabolism, obesity, hypertension and the like has been noted. This pathology involving plural risk factors attracts attention as "metabolic syndrome" or "multiple risk factor syndrome". With regard to this pathology, a treatment of hyperlipidemia, hypertension and obesity is required in addition to the control of plasma glucose level. In this pathology, moreover, thrombus may be easily developed due to the increased blood viscosity. Hence, a pharmaceutical agent suppressing thrombus formation, i.e., an antiplatelet drug or an anticoagulant, may also be used in combination.

Glucagon-like peptide-1 (hereinafter sometimes to be referred to as GLP-1) and glucose-dependent insulinotropic peptide (hereinafter sometimes to be referred to as GIP), which are secreted from the gastrointestinal tract after a meal, have a strong insulin secretagogue effect. However, since GLP-1 and GIP are degraded by dipeptidyl peptidase IV (hereinafter sometimes to be referred to as DPP-IV), they may fail to exhibit the effect sufficiently in the living body.

A DPP-IV inhibitor promotes insulin secretion by suppressing degradation of GLP-1 and GIP, and shows a hypoglycemic effect. Thus, it is under development as a therapeutic drug for type 2 diabetes (see non-patent reference 1).

Moreover, a treatment method attempting to control plasma glucose by combining a DPP-IV inhibitor and other antidiabetic drug is known (see patent references 1, 2). Furthermore, a recent result has documented clinical studies of plasma glucose control by a combination of a DPP-IV inhibitor LAF237 and metformin (see non-patent reference 2).

However, all of these combinations are between a particular compound having a DPP-IV inhibitory effect and other antidiabetic drug, with no specific description of a combination of 3-{(2S,4S)-4-[4-(3-methyl-1-phenyl-1H-pyrazol-5-yl)piperazin-1-yl]pyrrolidin-2-ylcarbonyl}thiazolidine, a salt of the compound with an organic or inorganic mono- or di-basic acid or a solvate thereof, as a DPP-IV inhibitor, and other antidiabetic drug, and a therapeutic effect on diabetes afforded by the combination is not known at all.

patent reference 1: WO01/052825
patent reference 2: WO01/097808
non-patent reference 1: Drucker D J, Expert Opin Investig Drugs 2003, 12: 87-100
non-patent reference 2: Ahren B et al., Diabetes Care. 2004, 27:2874-80

DISCLOSURE OF THE INVENTION

Problems to be Solved by the Invention

The problem to be solved by the present invention is provision of a superior pharmaceutical agent for the treatment of type 2 diabetes, which is yet to be established, and a treatment method using the same.

Means of Solving the Problems

The present inventors have conducted intensive studies in view of the above and found that an appropriate plasma glucose control is enabled by combining 3-{(2S,4S)-4-[4-(3-methyl-1-phenyl-1H-pyrazol-5-yl)piperazin-1-yl]pyrrolidin-2-ylcarbonyl}thiazolidine, a salt of the compound with an organic or inorganic mono- or di-basic acid or a solvate thereof and, for example, an antidiabetic drug such as metformin, voglibose and the like. They have studied the combination in detail, and also found that a combination with an α-glucosidase inhibitor such as voglibose and the like affords a hypoglycemic effect which is almost free of induction of insulin secretion.

Effect of the Invention

The concomitant agent of the present invention is effective as a drug for the treatment and/or prophylaxis of type 2 diabetes, diabetic complications and the like, and can be administered for the prophylaxis, delayed progress or treatment of, for example, hyperglycemia, hyperinsulinemia, hyperlipidemia, hypertriglyceridemia, diabetes, an insulin resistant glucose metabolism disorder, an impaired glucose tolerance (hereinafter sometimes to be also referred to as IGT) condition, an impaired fasting plasma glucose condition, obesity, diabetic retinopathy, diabetic nephropathy, glomerulosclerosis, diabetic neuropathy, metabolic syndrome, a coronary heart disease, chronic and acute renal failure or hypertension and the like in warm-blooded mammals represented by human. Particularly, since a combination of 3-{(2S,4S)-4-[4-(3-methyl-1-phenyl-1H-pyrazol-5-yl)piperazin-1-yl]pyrrolidin-2-ylcarbonyl}thiazolidine and an α-glucosidase inhibitor shows a hypoglycemic effect without accompanying insulin secretion, it provides a new treatment method of diabetes.

BEST MODE FOR EMBODYING THE INVENTION

Figure 1:
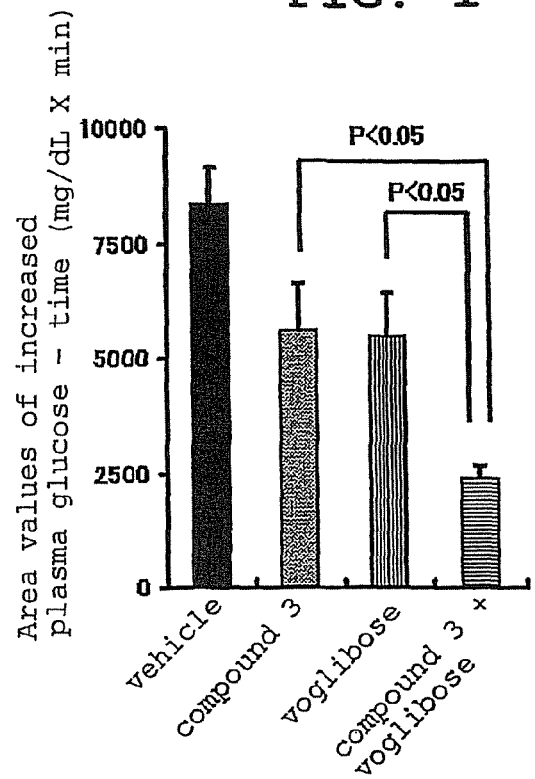
FIG. 1 The Figure shows the effect of compound 3 and voglibose on area values of increased plasma glucose concentration-time after oral carbohydrate loading, as well as the effect of a combination of compound 3 and voglibose in ZF rat. Each column shows mean±standard error. The time area value was calculated from the changes in the plasma glucose level for 60 min after carbohydrate loading. *$P<0.05$: comparison between compound 3 or voglibose alone (group 2 or 3) and combined use (group 4) (Student's t-test).

That is, the present invention relates to the concomitant agents described in the following (1) to (12) and the prophylactic and/or therapeutic methods described in (13) to (23).

(1). A concomitant agent to be used simultaneously or separately, comprising a combination of (a) 3-{(2S,4S)-4-[4-(3-methyl-1-phenyl-1H-pyrazol-5-yl)piperazin-1-yl]pyrrolidin-2-ylcarbonyl}thiazolidine, a salt of the compound with an organic or inorganic and mono- or di-basic acid or a solvate thereof, and (b) at least one kind of active ingredient selected from the group consisting of an active ingredient of a pharmaceutical agent selected from (i) an antidiabetic drug, (ii) a lipid lowering drug, (iii) an antihypertensive drug, (iv) a therapeutic drug for diabetic complications, (v) an antiobesity drug, (vi) an antiplatelet drug and (vii) an anticoagulant, a pharmaceutically acceptable salt thereof and a solvate thereof.

(2). A concomitant agent to be used simultaneously or separately, comprising a combination of (a) 3-{(2S,4S)-4-[4-(3-methyl-1-phenyl-1H-pyrazol-5-yl)piperazin-1-yl]pyrrolidin-2-ylcarbonyl}thiazolidine, a salt of the compound with an organic or inorganic and mono- or di-basic acid or a solvate thereof;

(b) at least one kind of active ingredient selected from the group consisting of an active ingredient of a pharmaceutical agent selected from (i) an antidiabetic drug, (ii) a lipid lowering drug, (iii) an antihypertensive drug, (iv) a therapeutic drug for diabetic complications, (v) an antiobesity drug, (vi) an antiplatelet drug and (vii) an anticoagulant, a pharmaceutically acceptable salt thereof and a solvate thereof; and (c) a pharmaceutically acceptable carrier.

(3). The concomitant agent of the aforementioned (1) or (2), wherein (b) is at least one kind of active ingredient selected from an active ingredient of a pharmaceutical agent selected from (i) an antidiabetic drug, (ii) a lipid lowering drug and (iii) an antihypertensive drug, a pharmaceutically acceptable salt thereof and a solvate thereof.

(4). The concomitant agent of any of the aforementioned (1) to (3), wherein the organic or inorganic and mono- or di-basic acid is hydrochloric acid, hydrobromide acid, nitric acid, mesylate, tosylate, besylate, maleic acid, naphthalene-1-sulfonic acid, naphthalene-2-sulfonic acid, gallic acid or camphorsulfonic acid.

(5). The concomitant agent of any of the aforementioned (1) to (4), wherein the organic or inorganic and mono- or di-basic acid is 2.0 hydrobromide acid, 2.5 hydrobromide acid, 2 maleic acid, 2 tosylate, 2.5 hydrochloric acid, 2 naphthalene-1-sulfonic acid, 2 mesylate, 3 mesylate or 2 naphthalene-2-sulfonic acid.

(6). The concomitant agent of any of the aforementioned (1) to (5), wherein the antidiabetic drug is at least one kind of active ingredient selected from the group consisting of an active ingredient of a pharmaceutical agent selected from insulin, an insulin secretagogue, an insulin sensitizer, an insulin signal transduction modulator, a pharmaceutical agent comprising, as an active ingredient, a compound influencing abnormal regulation of liver glucose production and a carbohydrate absorption inhibitor, a pharmaceutically acceptable salt thereof and a solvate thereof.

(7). The concomitant agent of the aforementioned (6), wherein the insulin secretagogue is a sulfonylurea agent, a non-sulfonylurea insulin secretagogue, an incretin hormone or a sodium ion-glucose co-transporter inhibitor, the insulin sensitizer is a thiazolidinedione derivative, a non-glitazone PPARγ agonist, a dual PPARα/γ agonist, a retinoid X receptor agonist or a 11β hydroxysteroid dehydrogenase type 1 inhibitor, the insulin signal transduction modulator is a protein tyrosine phosphatase inhibitor, a glutamine-fructose-6-phosphoric acid amidetransferase inhibitor, an antidiabetic non-small molecule mimetic compound, a GSK-3 inhibitor, a JNK inhibitor or an IKβ inhibitor, the pharmaceutical agent comprising, as an active ingredient, a compound influencing abnormal regulation of liver glucose production is a biguanide, a glucose-6-phosphatase inhibitor, a fructose-1,6-bisphosphatase inhibitor, a glycogen phosphorylase inhibitor, a glucagon receptor antagonist, a phosphoenolpyruvate carboxykinase inhibitor or a pyruvate dehydrogenasekinase inhibitor, and the carbohydrate absorption inhibitor is a stomach content excretion inhibitor or an α-glucosidase inhibitor.

(8). The concomitant agent of any of the aforementioned (1) to (5), wherein the lipid lowering drug is selected from the group consisting of a microsomal triglyceride transfer protein inhibitor, an HMG-CoA reductase inhibitor, an anion exchange resin, a cholesterol absorption inhibitor, a squalene synthase inhibitor, a cholesteryl ester transfer protein inhibitor, a fibric acid derivative, a drug controlling increase in LDL receptor activity, a lipoxygenase inhibitor and an ACAT inhibitor.

(9). The concomitant agent of any of the aforementioned (1) to (5), wherein the antihypertensive drug is selected from the group consisting of an ACE inhibitor, an AT1 receptor antagonist, a rennin inhibitor, an NEP/ACE inhibitor, a calcium channel antagonist, an α1-adrenoceptor blocker, a β-adrenoceptor blocker, a diuretic, an endothelin converting enzyme inhibitor and an endothelin receptor antagonist.

(10). The concomitant agent of any of the aforementioned (1) to (5), wherein the antidiabetic drug is at least one kind of active ingredient selected from the group consisting of glimepiride, glipizide, tolbutamide, chlorpropamide, tolazamide, acetohexamide, glyburide, repaglinide, nateglinide, mitiglinide, exenatide, NN-2211, CJC-1131, ZP-10, LY315902, pioglitazone, troglitazone, rosiglitazone, MCC-555, Gl-262570, JTT-501, muraglitazar, tesaglitazar, LY-465608, LG100268, LGD1069, BVT-3498, BVT-2773, BVT-14225, L-783281, metformin, CS-917, BAY27-9955, insulin, amylin, acarbose, voglibose, miglitol, T-1095 and KGA2727, pharmaceutically acceptable salts thereof and solvates thereof, the lipid lowering drug is at least one kind of active ingredient selected from the group consisting of implitapide, JTT-130, pravastatin, lovastatin, simvastatin, atorvastatin, pitavastatin, cerivastatin, fenofibrate, gemfibrozil, clofibrate, colestimide (colestilan), colestyramine resin, colestipol, sevelamer hydrochloride, colesevelam hydrochloride and ezetimibe, pharmaceutically acceptable salts thereof and solvates thereof, the antihypertensive drug is at least one kind of active ingredient selected from the group consisting of captopril, fosinopril, enalapril, lisinopril, quinapril, benazepril, fentiapril, ramipril, omapatrilat, fasidotril, irbesartan, losartan, valsartan, candesartan, telmisartan, olmesartan, amlodipine besylate, nifedipine, felodipine, nitrendipine, propranolol, metoprolol, atenolol, carvedilol, betaxolol, prazosin, terazosin, doxazosin, spironolactone and eplerenone, pharmaceutically acceptable salts thereof and solvates thereof, the therapeutic drug for diabetic complications is at least one kind of active ingredient selected from the group consisting of epalrestat, fidarestat, zenarestat, AS-3201, ruboxistaurin, ALT-946, MCC-257, TAK-428 and TAK-128, pharmaceutically acceptable salts thereof and solvates thereof, the antiobesity drug is at least one kind of active ingredient selected from the group consisting of YM-178, CL-316243, orlistat, cetilistat, sibutramine, mazindol and rimonabant, pharmaceutically acceptable salts thereof and solvates thereof, the antiplatelet drug is at least one kind of active ingredient selected from the group consisting of aspirin, clopidogrel, ticlopidine, dipyridamole, cilostazol, sarpogrelate, ozagrel and prasugrel, pharmaceutically acceptable salts thereof and solvates thereof, and the anticoagulant is at least one kind of active ingredient selected from the group consisting of warfarin, ximelagatran, aragatroban, low molecule heparin and MCC-977, pharmaceutically acceptable salts thereof and solvates thereof.

(11). The concomitant agent of any of the aforementioned (1) to (5), wherein (b) is at least one kind of active ingredient selected from the group consisting of metformin and an α-glucosidase inhibitor, pharmaceutically acceptable salts thereof and solvates thereof.

(12). The concomitant agent of any of the aforementioned (1) to (11), which is administered for the prophylaxis, delayed progress or treatment of hyperglycemia, hyperinsulinemia, hyperlipidemia, hypertriglyceridemia, diabetes, an insulin resistant glucose metabolism disorder, an impaired glucose tolerance condition, an impaired fasting plasma glucose condition, obesity, diabetic retinopathy, diabetic nephropathy, glomerulosclerosis, diabetic neuropathy, metabolic syndrome, a coronary heart disease, chronic and acute renal failure or hypertension to a warm-blooded mammal in need of such prophylaxis, delayed progress or treatment.

(13). The concomitant agent of any of the aforementioned (1) to (11), which is administered for the treatment to decrease a high plasma glucose level of a warm-blooded mammal without causing insulin secretion.

(14). A method for preventing and/or treating hyperglycemia, hyperinsulinemia, hyperlipidemia, hypertriglyceridemia, diabetes, an insulin resistant glucose metabolism disorder, an impaired glucose tolerance condition, an impaired fasting plasma glucose condition, obesity, diabetic retinopathy, diabetic nephropathy, glomerulosclerosis, diabetic neuropathy, metabolic syndrome, a coronary heart disease, chronic or acute renal failure or hypertension, which comprises administrating at least one kind of active ingredient selected from the group consisting of (a) 3-{(2S,4S)-4-[4-(3-methyl-1-phenyl-1H-pyrazol-5-yl)piperazin-1-yl]pyrrolidin-2-ylcarbonyl}thiazolidine, a salt of the compound with an organic or inorganic and mono- or di-basic acid or a solvate thereof, and (b) at least one kind of active ingredient selected from the group consisting of an active ingredient of a pharmaceutical agent selected from (i) an antidiabetic drug, (ii) a lipid lowering drug, (iii) an antihypertensive drug, (iv) a therapeutic drug for diabetic complications, (v) an antiobesity drug, (vi) an antiplatelet drug and (vii) an anticoagulant, a pharmaceutically acceptable salt thereof and a solvate thereof.

(15). The method of the aforementioned (14), wherein (b) is at least one kind of active ingredient selected from an active ingredient of a pharmaceutical agent selected from (i) an antidiabetic drug, (ii) a lipid lowering drug and (iii) an antihypertensive drug, a pharmaceutically acceptable salt thereof and a solvate thereof.

(16). The method of the aforementioned (14) or (15), wherein the organic or inorganic and mono- or di-basic acid is hydrochloric acid, hydrobromide acid, nitric acid, mesylate, tosylate, besylate, maleic acid, naphthalene-1-sulfonic acid, naphthalene-2-sulfonic acid, gallic acid or camphorsulfonic acid.

(17). The method of any of the aforementioned (14) to (16), wherein the organic or inorganic and mono- or di-basic acid is 2.0 hydrobromide acid, 2.5 hydrobromide acid, 2 maleic acid, 2 tosylate, 2.5 hydrochloric acid, 2 naphthalene-1-sulfonic acid, 2 mesylate, 3 mesylate or 2 naphthalene-2-sulfonic acid.

(18). The method of any of the aforementioned (14) to (17), wherein the antidiabetic drug is at least one kind of active ingredient selected from the group consisting of an active ingredient of a pharmaceutical agent selected from insulin, an insulin secretagogue, an insulin sensitizer, an insulin signal transduction modulator, a pharmaceutical agent comprising, as an active ingredient, a compound influencing abnormal regulation of liver glucose production and a carbohydrate absorption inhibitor, a pharmaceutically acceptable salt thereof and a solvate thereof.

(19). The method of the aforementioned (18), wherein the insulin secretagogue is a sulfonylurea agent, a non-sulfonylurea insulin secretagogue, an incretin hormone or a sodium ion-glucose co-transporter inhibitor, the insulin sensitizer is a thiazolidinedione derivative, a non-glitazone PPARγ agonist, a dual PPARα/γ agonist, a retinoid X receptor agonist or a 11β hydroxysteroid dehydrogenase type 1 inhibitor, the insulin signal transduction modulator is a protein tyrosine phosphatase inhibitor, a glutamine-fructose-6-phosphoric acid amidetransferase inhibitor, an antidiabetic non-small molecule mimetic compound, a GSK-3 inhibitor, a JNK inhibitor or an IKβ inhibitor, the pharmaceutical agent comprising, as an active ingredient, a compound influencing abnormal regulation of liver glucose production is a biguanide, a glucose-6-phosphatase inhibitor, a fructose-1,6-bisphosphatase inhibitor, a glycogen phosphorylase inhibitor, a glucagon receptor antagonist, a phosphoenolpyruvate carboxykinase inhibitor or a pyruvate dehydrogenasekinase inhibitor, and
the carbohydrate absorption inhibitor is a stomach content excretion inhibitor or an α-glucosidase inhibitor.
(20). The method of any of the aforementioned (14) to (17), wherein the lipid lowering drug is selected from the group consisting of a microsomal triglyceride transfer protein inhibitor, an HMG-CoA reductase inhibitor, an anion exchange resin, a cholesterol absorption inhibitor, a squalene synthase inhibitor, a cholesteryl ester transfer protein inhibitor, a fibric acid derivative, a drug controlling increase in LDL receptor activity, a lipoxygenase inhibitor and an ACAT inhibitor.
(21). The method of any of the aforementioned (14) to (17), wherein the antihypertensive drug is selected from the group consisting of an ACE inhibitor, an AT1 receptor antagonist, a rennin inhibitor, an NEP/ACE inhibitor, a calcium channel antagonist, an α1-adrenoceptor blocker, a β-adrenoceptor blocker, a diuretic, an endothelin converting enzyme inhibitor and an endothelin receptor antagonist.
(22). The method of any of the aforementioned (14) to (17), wherein the antidiabetic drug is at least one kind of active ingredient selected from the group consisting of glimepiride, glipizide, tolbutamide, chlorpropamide, tolazamide, acetohexamide, glyburide, repaglinide, nateglinide, mitiglinide, exenatide, NN-2211, CJC-1131, ZP-10, LY315902, pioglitazone, troglitazone, rosiglitazone, MCC-555, Gl-262570, JTT-501, muraglitazar, tesaglitazar, LY-465608, LG100268, LGD1069, BVT-3498, BVT-2773, BVT-14225, L-783281, metformin, CS-917, BAY27-9955, insulin, amylin, acarbose, voglibose, miglitol, T-1095 and KGA2727, pharmaceutically acceptable salts thereof and solvates thereof,
the lipid lowering drug is at least one kind of active ingredient selected from the group consisting of implitapide, JTT-130, pravastatin, lovastatin, simvastatin, atorvastatin, pitavastatin, cerivastatin, fenofibrate, gemfibrozil, clofibrate, colestimide (colestilan), colestyramine resin, colestipol, sevelamer hydrochloride, colesevelam hydrochloride and ezetimibe, pharmaceutically acceptable salts thereof and solvates thereof,
the antihypertensive drug is at least one kind of active ingredient selected from the group consisting of captopril, fosinopril, enalapril, lisinopril, quinapril, benazepril, fentiapril, ramipril, omapatrilat, fasidotril, irbesartan, losartan, valsartan, candesartan, telmisartan, olmesartan, amlodipine besylate, nifedipine, felodipine, nitrendipine, propranolol, metoprolol, atenolol, carvedilol, betaxolol, prazosin, terazosin, doxazosin, spironolactone and eplerenone, pharmaceutically acceptable salts thereof and solvates thereof,
the therapeutic drug for diabetic complications is at least one kind of active ingredient selected from the group consisting of epalrestat, fidarestat, zenarestat, AS-3201, ruboxistaurin, ALT-946, MCC-257, TAK-428 and TAK-128, pharmaceutically acceptable salts thereof and solvates thereof,
the antiobesity drug is at least one kind of active ingredient selected from the group consisting of YM-178, CL-316243, orlistat, cetilistat, sibutramine, mazindol and rimonabant, pharmaceutically acceptable salts thereof and solvates thereof,
the antiplatelet drug is at least one kind of active ingredient selected from the group consisting of aspirin, clopidogrel, ticlopidine, dipyridamole, cilostazol, sarpogrelate, ozagrel and prasugrel, pharmaceutically acceptable salts thereof and solvates thereof, and
the anticoagulant is at least one kind of active ingredient selected from the group consisting of warfarin, ximelagatran, aragatroban, low molecule heparin and MCC-977, pharmaceutically acceptable salts thereof and solvates thereof.
(23). The method of any of the aforementioned (14) to (17), wherein (b) is at least one kind of active ingredient selected from the group consisting of metformin and an α-glucosidase inhibitor, pharmaceutically acceptable salts thereof and solvates thereof.

The definitions of the terms in the present specification are shown below. However, the following definitions do not limit the scope of the present invention. "3-{(2S,4S)-4-[4-(3-methyl-1-phenyl-1H-pyrazol-5-yl)piperazin-1-yl]pyrrolidin-2-ylcarbonyl}thiazolidine (hereinafter to be indicated as compound 2)" is a compound represented by the following chemical formula (2).

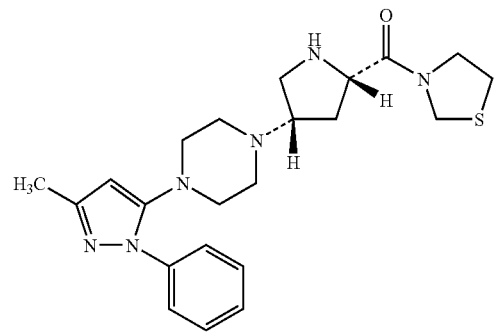

(2)

The 3 hydrochloride of compound 2 can be produced according to the synthesis method described as Example 222 of WO 02/14271. In addition, this can be converted to compound 2 using a suitable base. Compound 2, a salt of the compound with an organic or inorganic and mono- or di-basic acid or a solvate thereof, which is the active ingredient of the concomitant drug of the present invention, can be formed by converting compound 2 to various novel salt forms according to a conventional method.

The "mono- or di-basic acid" is an acid capable of donating 1 or 2 protons, and the mono- or di-basic acid may be an organic acid or inorganic acid. Examples of the "organic or inorganic and mono- or di-basic acid" include hydrochloric acid, hydrobromic acid, nitric acid, mesylate, tosylate, besylate, maleic acid, naphthalene-1-sulfonic acid, naphthalene-2-sulfonic acid, gallic acid, camphorsulfonic acid and the like. Preferred are hydrochloric acid, hydrobromic acid, maleic acid, mesylate, tosylate, naphthalene-1-sulfonic acid, 2-naphthalene-2-sulfonic acid and the like.

The "solvate" is a compound wherein a solvent is bonded, and when the solvent is water, the solvate may sometimes be particularly referred to as hydrate. A salt as an active ingredient in the concomitant drug of the present invention may be present as any solvate, and hydrate is more preferable. The "antidiabetic drug" means a pharmaceutical agent containing a biological substance such as insulin and the like as an active ingredient, an insulin secretagogue that promotes insulin secretion from pancreatic β-cell, an insulin sensitizer or insulin signal transduction modulator that increases the insulin sensitivity by recovering the impaired insulin reactivity, a pharmaceutical agent containing, as an active ingredient, a compound influencing abnormal regulation of liver glucose production, a carbohydrate absorption inhibitor inhibiting absorption of carbohydrate from the gastrointestinal tract, and the like.

Specifically, a pharmaceutical agent containing a biological substance as an active ingredient [insulin etc.], an insulin secretagogue [sulfonylurea agent, non-sulfonylurea insulin secretagogue, incretin hormone, sodium-dependent glucose transporter (hereinafter to be referred to as SGLT) inhibitor etc.], an insulin sensitizer [thiazolidinedione derivative (hereinafter to be referred to as glitazone), a non-glitazone PPARγ agonist, a dual PPARα/γ agonist, a retinoid X receptor (hereinafter to be referred to as RXR) agonist, a 11β hydroxysteroid dehydrogenase type 1 (hereinafter to be referred to as 11β-HSD1) inhibitor etc.], an insulin signal transduction modulator [protein tyrosine phosphatase (hereinafter to be referred to as PRPase) inhibitor, glutamine-fructose-6-phosphate amidotransferase (hereinafter to be referred to as GFAT) inhibitor, antidiabetic non-small molecule mimetic compound, GSK-3 inhibitor, JNK inhibitor, IKβ inhibitor etc.], a pharmaceutical agent containing, as active ingredient, a compound influencing abnormal regulation of liver glucose production [biguanide, glucose-6-phosphatase (G6Pase) inhibitor, fructose-1,6-bisphosphatase (F-1,6-BPase) inhibitor, glycogen phosphorylase (hereinafter to be referred to as GP) inhibitor, glucagon receptor antagonist, phosphoenolpyruvate carboxykinase (hereinafter to be referred to as PEPCK) inhibitor, pyruvate dehydrogenasekinase (hereinafter to be referred to as PDHK) inhibitor etc.], a carbohydrate absorption inhibitor [stomach content excretion inhibitor, α-glucosidase inhibitor etc.] and the like can be mentioned.

Of the specific examples of the pharmaceutical agent containing a biological substance per se as an active ingredient, examples of the "insulin and the like" include Berlinsulin (Berlin-Chemie), Huminsulin (Eli Lilly), Insulin Actrapid (Novo Nordisk), Insuman (Aventis) and the like. Specific examples of the insulin secretagogue include the following respective drug groups.

Examples of the "sulfonylurea agent" include glimepiride, glipiride, tolbutamide, chlorpropamide, tolazamide, acetohexamide, 4-chloro-N-[(1-pyrrolidinylamino)carbonyl]-benzenesulfoneamide (glycopyramide), glibenclamide (glyburide), gliclazide, 1-butyl-3-metanilylurea, carbutamide, glibonuride, glipizide, gliquidone, glisoxepid, glybuthiazole, glybuzole, glyhexamide, glymidine, glypinamide, phenbutamide, tolylcyclamide and the like, and pharmaceutically acceptable salts thereof.

Examples of the "non-sulfonylurea insulin secretagogue" include nateglinide, mitiglinide, repaglinide and the like and pharmaceutically acceptable salts thereof.

Examples of the "incretin hormone" include GLP-1, and GLP-1 agonist and the like. Here, the "GLP-1" is, for example, an insulin secretion enhancing protein described in U.S. Pat. No. 5,705,483. In addition, the "GLP-1 agonist" means variant, analog and the like of GLP-1(7-36)NH2 particularly described in U.S. Pat. No. 5,120,712, U.S. Pat. No. 5,118,666 and U.S. Pat. No. 5,512,549 and WO 91/11457. It is particularly a compound such as GLP-1(7-37), a compound wherein carboxy terminal amide functional group of Arg36 is substituted by Gly at the 37-position of GLP-1(7-36)NH2 molecule, a variant thereof and an analog thereof, such as GLN9-GLP-1(7-37), D-GLN9-GLP-1(7-37), acetyl LYS9-GLP-1(7-37), LYS18-GLP-1(7-37) and particularly including GLP-1(7-37)OH, VAL8-GLP-1(7-37), GLY8-GLP-1(7-37), THR8-GLP-1(7-37), MET8-GLP-1(7-37) and 4-imidazopropionyl-GLP-1. In addition, particularly preferred are exenatide, NN-2211, CJC-1131, ZP-10, LY315902 and the like.

Examples of the "sodium-dependent glucose transporter (SGLT) inhibitor" include T-1095, KGA2727 and the like.

More specific examples of the insulin sensitizer include the following respective drug groups.

Examples of the "thiazolidinedione derivative (glitazone)" include isaglitazone, (S)-((3,4-dihydro-2-(phenyl-methyl)-2H-1-benzopyran-6-yl)methyl-thiazolidine-2,4-dione (eneglitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy]-phenyl}methyl)-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108), 5-{[4-(2-(2,3-dihydroindol-1-yl)ethoxy)phenyl]methyl}-thiazolidine-2,4-dione, 5-[3-(4-chloro-phenyl)]-2-propynyl]-5-phenylsulfonyl)thiazolidine-2,4-dione, 5-[3-(4-chlorophenyl)]-2-propynyl]-5-(4-fluorophenyl-sulfonyl)thiazolidine-2,4-dione, 5-{[4-(2-(methyl-2-pyridinyl-amino)ethoxy)phenyl]methyl}-thiazolidine-2,4-dione (rosiglitazone), 5-{[4-(2-(5-ethyl-2-pyridyl)ethoxy)phenyl]-methyl}-thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC-555), 5-{[2-(2-naphthyl)-benzooxazol-5-yl]-methyl}thiazolidine-2,4-dione (T-174) or 5-(2,4-dioxothiazolidin-5-ylmethyl)-2-methoxy-N-(4-trifluoromethyl-benzyl)benzamido (KRP297) and the like. More preferred are, for example, pioglitazone, rosiglitazone, troglitazone and the like.

Examples of the "non-glitazone PPARγ agonist" include N-(2-benzoylphenyl)-L-tyrosine analog, and more specifically, GI-262570, JTT501 and the like can be mentioned.

The "dual PPARα/γ agonist" means a compound which is simultaneously PPARγ and PPARα agonists. Preferable examples of the dual PPARγ/PPARα agonist include muraglitazar, tesaglitazar, naveglitazar, LY-465608, ω-[(oxoquinazolinylalkoxy)phenyl]alkanoate and analog thereof, compound NN622 described in Example 22 of U.S. Pat. No. 6,054,453, compound DRF-554158 (sometimes to be referred to as DRF4158), compound NC-2100 (Fukui, Diabetes 2000, 49(5), 759-767) and the like.

The "retinoid X receptor (RXR) agonist" means, according to the measurement by a detection method known to those of ordinary skill in the art (described in U.S. Pat. No. 4,981,784, U.S. Pat. No. 5,071,773, U.S. Pat. No. 5,298,429 and U.S. Pat. No. 5,506,102, WO89/05355, WO91/06677, WO92/05447, WO93/11235, WO95/18380 and the like), "co-transfection" or "cis-trans" detection method and the like, a compound or composition that increases the transcription regulatory activity of RXR when combined with RXR homodimer or heterodimer. It includes a compound that preferentially activates RXR rather than RAR (that is, RXR specific agonist) and a compound that activates both RXR and RAR (that is, pan agonist). In addition, it also includes a compound that activates RXR rather than others under certain cell conditions (i.e., partial agonist).

Examples of the "RXR agonist" include compounds described in U.S. Pat. No. 5,399,586, U.S. Pat. No. 5,466,861, WO96/05165, WO94/15901, WO93/11755, WO94/15902 and WO93/21146 and the like.

Examples of the "RXR specific agonist" include 2-[1-(3,5,5,8,8-pentamethyl-5,6,7,8-tetrahydro-2-naphthyl)-cyclopropyl]pyridine-5-carboxylic acid (LG100268), 4-[(3,5,5,8,8-pentamethyl-5,6,7,8-tetrahydro-2-naphthyl)-2-carbonyl]-benzoic acid (LGD1069), analogs thereof, derivatives thereof, pharmaceutically acceptable salts thereof and the like. The structures and syntheses of LG100268 and LGD1069 are described in Boehm et al., J. Med. Chem. 38, 3146-3155, 1995.

Examples of the "pan agonist" include alitretinoin (pan retine), analogs thereof, derivatives thereof, pharmaceutically acceptable salts thereof and the like.

Examples of the "11β hydroxysteroid dehydrogenase type 1 inhibitor" include BVT-3498, BVT-2773, BVT-14225 and compounds described in U.S. Pat. No. 6,849,636, WO 2003/65983, WO 2003/104208, WO 2004/106294, WO 2005/16877, WO 2004/11410, WO 2004/33427, WO 2004/41264, WO 2004/56745, WO 2004/65351, WO 2004/89471, WO 2004/89896 and WO 2005/44192 and the like.

As specific examples of the insulin signal transduction modulator, the following respective drug groups can be mentioned.

Examples of the "protein tyrosine phosphatase (PTPase) inhibitor" include compounds described in U.S. Pat. No. 6,057,316, U.S. Pat. No. 6,001,867, WO 99/58518, WO 99/58522, WO 99/46268, WO 99/46267, WO 99/46244, WO 99/46237, WO 99/46236 and WO 99/15529 and the like.

Examples of the "glutamine-fructose-6-phosphate amidotransferase (GFAT) inhibitor" include a compound described in Mol. Cell. Endocrinol. 1997, 135(1), 67-77 and the like.

Examples of the "antidiabetic non-small molecule mimetic compound" include compounds described in Science 1999, 284, 974-97, particularly L-783281, CLX-901 and WO 99/58127 and the like.

Examples of the "inhibitor of GSK-3" include compounds described in WO 00/21927 and WO 97/41854 and the like.

As specific examples of the pharmaceutical agent containing, as an active ingredient, a compound influencing abnormal regulation of liver glucose production, the following respective drug groups can be mentioned.

Examples of the "biguanide" include metformin, buformin, phenformin and the like.

The "glucose-6-phosphatase (G6Pase) inhibitor" means a compound or composition that decreases or inhibits liver gluconeogenesis by decreasing or inhibiting G6Pase activity, and the like. Examples of preferable compound include compounds described in WO 00/14090, WO 99/40062, WO 98/40385, EP-B-682024 and Diabetes 1998, 47, 1630-1636 and the like.

The "fructose-1,6-bisphosphatase (F-1,6-BPase) inhibitor" means a compound or composition that decreases or inhibits liver gluconeogenesis by decreasing or inhibiting F-1,6-Bpase activity, and the like. Examples of preferable compound include CS-917, compounds described in WO 00/14095, WO 99/47549, WO 98/39344, WO 98/39343 and WO 98/39342 and the like.

The "glycogen phosphorylase (GP) inhibitor" means a compound or composition that decreases or inhibits liver gluconeogenesis by decreasing or inhabiting GP activity, and the like. Examples of preferable compound include compounds described in EP-B-978279, U.S. Pat. No. 5,998,463, EP-B-846464, WO 99/26659, WO 97/31901, WO 96/39384, WO 96/39385 and CP-91149 described in Proc. Natl. Acad. Sci USA 1998, 95, 1776-1781 and the like.

Examples of the "glucagon receptor antagonists" include a compound described in WO 98/04528 and the like, particularly BAY27-9955. In addition, a compound described in Bioorg. Med. Chem. Lett. 1992, 2, 915-918 and the like can be mentioned. More specifically, CP-99711, a compound described in J. Med. Chem. 1998, 41, 5150-5157, NNC92-1687, a compound described in J. Biol. Chem. 1999, 274, 8694-8697, L-168049, compounds described in U.S. Pat. No. 5,880,139, U.S. Pat. No. 5,776,954, WO99/01423, WO98/22109, WO98/22108, WO98/21957 and WO 97/16442 and the like can be mentioned.

The "phosphoenolpyruvate carboxykinase (PEPCK) inhibitor" means a compound or composition that decreases or inhibits liver gluconeogenesis by decreasing or inhibiting PEPCK activity, and the like. Examples of preferable compound include compounds described in U.S. Pat. No. 6,030,837 and Mol. Biol. Diabetes 1994, 2, 283-99 and the like.

Examples of the "pyruvate dehydrogenase kinase (PDHK) inhibitor" include a compound described in Aicher et al., J. Med. Chem. 1999, 42, 2741-2746 and the like.

As specific examples of carbohydrates absorption inhibitor, the following respective drug groups can be mentioned.

Examples of the "stomach content excretion inhibitor" include CCK-8 and a compound described in Diabetes Care 1998, 21, 897-893 and the like, and particularly, amylin and analog thereof, for example, pramlintide and the like are preferable. Amylin is described in, for example, O. G. Kolterman et al., Diabetologia 1996, 3, 492-499.

Examples of the "α-glucosidase inhibitor" include voglibose, acarbose, miglitol and the like. Miglitol is described in U.S. Pat. No. 4,639,436. Miglitol can be administered, for example, in a commercially available dosage form such as registered trade mark DIASTABOL 50 (DIASTABOL, registered trade mark).

The "lipid lowering drug" is a pharmaceutical agent that decreases cholesterol (particularly, LDL-cholesterol) and neutral fats in blood and/or increases HDL in blood. Specific examples include microsomal triglyceride transfer protein (hereinafter sometimes to be referred to as MTP) inhibitor, HMG-CoA reductase inhibitor, anion exchange resin, cholesterol absorption inhibitor, squalene synthase inhibitor, cholesteryl ester transfer protein inhibitor, fibric acid derivative, a drug controlling increase in LDL receptor activity, lipoxygenase inhibitor, ACAT inhibitor and the like.

As specific examples of lipid lowering drug, the following respective drug groups can be mentioned.

Examples of the "MTP inhibitor" include implitapide (BAY-13-9952), CP-346086, JTT-130, BMS-212122, GR-328713 and the like.

Examples of the "HMG-CoA reductase inhibitor" include pravastatin, lovastatin, simvastatin, fluvastatin, atorvastatin, pitavastatin, cerivastatin, itavastatin, visastatin, preferably pravastatin, lovastatin, simvastatin, a pharmaceutically acceptable salt thereof and the like.

Examples of the "anion exchange resin" include colestimide (colestilan), colestyramine resin, colestipol, sevelamer hydrochloride, colesevelam hydrochloride and the like.

Examples of the "cholesterol absorption inhibitor" include ezetimibe and the like.

Examples of the "squalene synthase inhibitor" include TAK-475 and the like.

Examples of the "cholesteryl ester transfer protein inhibitor" include JTT-705 and the like.

As the "fibric acid derivative", a commercially available drug is preferable, and fenofibrate, gemfibrozil, clofibrate and the like are more preferable.

Examples of the "ACAT inhibitory" include pactimibe, avasimibe, eflucimibe, CS-505, SR-45023A, SMP-797, K-604, TS-962 and the like.

The "antihypertensive drug" is a pharmaceutical agent that decreases blood pressure by suppressing production of a biological substance that increases the blood pressure (hormone or protein increasing circulatory blood flow, or hormone or protein having an effect to potentiate vasoconstriction or myocardial contraction etc.), or competing with the biological substance. Examples thereof include angiotensin converting enzyme inhibitor (hereinafter to be sometimes referred to as ACE inhibitor), angiotensin II type 1 (hereinafter to be sometimes referred to as AT1) receptor antagonist, rennin inhibitor, NEP/ACE inhibitor, calcium channel antagonist, α1-adrenoceptor blocker, β-adrenoceptor blocker, diuretic (mineral corticoid receptor antagonist) and the like.

As specific examples of the antihypertensive drug, the following respective drug groups can be mentioned.

Examples of the "ACE inhibitor" include a compound selected from the group consisting of alacepril (EP-B-7477), benazepril (EP-B-72352), benazeprilat (EP-B-72352), captopril (U.S. Pat. No. 4,105,776), ceronapril (EP-B-229520), cilazapril (EP-B-94095), delapril (EP-B-51391), enalapril (EP-B-12401), enaprilat (EP-B-12401), fosinopril (EP-B-53902), imidapril (EP-B-95163), lisinopril (EP-B-12401), moveltipril (South Africa-B-82/3779), perindopril (EP-B-49658), quinapril (EP-B-49605), ramipril (EP-B-79022), spirapril (see EP-B-50800), temocapril (EP-B-161801) and trandolapril (EP-B-551927), a pharmaceutically acceptable salt thereof and the like. Preferable ACE inhibitor is a commercially available drug, and more preferred are benazepril, enalapril, lisinopril and the like. An active ingredient corresponding to these or a pharmaceutically acceptable salt thereof can be used as a solvate to be used for crystallization, such as hydrate.

Examples of the "AT1 receptor antagonists" include a compound selected from the group consisting of valsartan, losartan, candesartan, eprosartan, irbesartan, saprisartan, tasosartan, telmisartan, olmesartan, a pharmaceutically acceptable salt thereof and the like. More preferred are valsartan, candesartan, a pharmaceutically acceptable salt thereof and the like.

Examples of the "rennin inhibitor" include, particularly, a corresponding non-peptidic inhibitor, preferably 2(S),4(S),5(S),7(S)—N-(3-amino-2,2-dimethyl-3-oxopropyl)-2,7-di(1-methylethyl)-4-hydroxy-5-amino-8-[4-methoxy-3-(3-methoxy-propoxy)phenyl]-octaneamide (aliskiren, specifically described in EP-A-678503) and the like, preferably hemifumarate thereof, detikiren (EP-A-173481), terlakiren (EP-A-266950), and zankiren (EP-A-229667), particularly preferably, aliskiren, hemi-fumarate thereof and the like.

Examples of the "NEP/ACE inhibitor" include omapatrilat, MDL100240, fasidotril, GW796406, a pharmaceutically acceptable salt thereof and the like.

Examples of the "calcium channel antagonist" include a compound selected from the group consisting of verapamil, nifedipine, diltiazem, azelnidipine, lercanidipine, nitrendipine, a pharmaceutically acceptable salt thereof and the like. Preferred are amlodipine besylate, nifedipine, felodipine, a pharmaceutically acceptable salt thereof and the like.

Examples of the "α1-adrenoceptor blocker" include a compound selected from the group consisting of prazosin and terazosin, a pharmaceutically acceptable salt thereof and the like. Preferred are doxazosin, a pharmaceutically acceptable salt thereof and the like.

Examples of the "β-adrenoceptor blocker" include a compound selected from the group consisting of propanolol, betaxolol, atenolol, a pharmaceutically acceptable salt thereof and the like. Preferred are metoprolol, atenolol, carvedilol, a pharmaceutically acceptable salt thereof and the like.

Examples of the "diuretic" include mineral corticoid receptor antagonist such as spironolactone, eplerenone etc. and the like.

The "therapeutic drug for diabetic complications" means a pharmaceutical agent that treats a chronic disease occurring in association with diabetes, such as diabetic retinopathy, diabetic nephropathy, diabetic neuropathy, arteriosclerosis and the like. As a therapeutic drug for diabetic neuropathy and diabetic retinopathy, Protein kinase C-β (PKC-β) inhibitor and the like can be mentioned, as a therapeutic drug for diabetic nephropathy, the aforementioned AT1 receptor antagonist and the like can be mentioned, and as a therapeutic drug for diabetic neuropathy, aldose reductase inhibitor and the like can be mentioned.

As specific examples of the therapeutic drug for diabetic complications, the following respective drug groups can be mentioned.

Examples of the "PKC-β inhibitor" include ruboxistaurin (LY-333531) and the like.

Examples of the "aldose reductase inhibitor" include epalrestat, fidarestat, zenarestat, AS-3201, NA-314, a pharmaceutically acceptable salt thereof and the like.

Examples of other therapeutic drug for diabetic complications include ALT-946, MCC-257, TAK-428, TAK-128 and the like.

The "antiobesity drug" is a pharmaceutical agent that suppresses inappropriate body weight gain or visceral fat increase, and examples thereof include β3 adrenergic agonist, lipase inhibitor, serotonin reuptake inhibitor (serotonin reuptake inhibitor in the present specification encompasses dopamine reuptake inhibitor), thyroid receptor agonist, aP2 inhibitor, feeding deterrent and the like.

As specific examples of the antiobesity drug, the following respective drug groups can be mentioned.

Examples of the "β3 adrenergic agonist" include YM-178, CL-316243 (Lederle Laboratories), compounds described in WO 99/29672, WO 98/32753, WO 98/20005, WO 98/09625, WO 97/46556, WO 97/37646 and U.S. Pat. No. 5,705,515 and the like.

Examples of the "lipase inhibitor" include orlistat, cetilistat (ATL-962) and the like.

The feeding deterrent is a pharmaceutical agent that suppresses appetite by inhibiting serotonin and noradrenaline reuptake or antagonizing cannabinoid receptor, and specific examples thereof include sibutramine (central anorectic effect), mazindol (trade name: Sanorex), rimonabant and the like.

The "antiplatelet drug" is a pharmaceutical agent that suppresses platelet coagulation ability and inhibits thrombus formation by platelets. Examples thereof include aspirin, clopidogrel, ticlopidine, dipyridamole, cilostazol, sarpogrelate, ozagrel, prasugrel and the like.

The "anticoagulant" is a pharmaceutical agent that suppresses the function of coagulation factor and inhibits thrombus formation. Examples thereof include warfarin, ximelagatran, aragatroban, low molecule heparin, MCC-977 and the like. The active ingredients exemplified above can be present in each case as a free form, a pharmaceutically acceptable salt or a solvate thereof.

The "at least one kind of active ingredient" means one or more, preferably two or three kinds, from one or more, preferably two or three groups, of active ingredients other than compound 2.

The "concomitant drug" in the claims of this application characteristically comprises compound 2, a salt with the compound and organic or inorganic and mono- or di-basic acid or a solvate thereof, and the above-mentioned "at least one kind of active ingredient". Particularly preferably, a combination of compound 2, a salt with organic or inorganic and mono- or di-basic acid or a solvate thereof, and metformin or voglibose can be mentioned.

In the concomitant drug of the present invention, an active ingredient thereof may be contained in separate preparations as plural preparations, or contained in one preparation as a single preparation.

The "simultaneous use" means a state where plural pharmaceutical agents or active ingredients thereof are substantially simultaneously administered to patients. Preferably, plural pharmaceutical agents or active ingredients thereof may be formulated into one preparation, or two or more preparations are at least substantially simultaneously administered, for example, in about 1 hr from each other.

The "separate use" means a state where plural pharmaceutical agents or active ingredients thereof are administered to patients in any order. The plural pharmaceutical agents or active ingredients thereof may be administered in the same number of times or different number of times. Specifically, one may be administered first and the other alone may be administered plural times to patients at given intervals, and the like.

The pharmaceutical activity exhibited by the administration of the concomitant drug of the present invention can be demonstrated, for example, using corresponding pharmacological models known in the pharmaceutical field. Those of ordinary skill in the art should be able to sufficiently establish the indication of treatment and beneficial effects mentioned above and those to be mentioned below, using the relevant animal test models. Therefore, the concomitant drug of the present invention can be used, for example, for the prophylaxis, delayed progress or treatment of disease, symptom and disorder mentioned above and those to be mentioned below.

That is, "cardiovascular disease or disorder" such as hypertension, congestive heart failure, diabetes, glomerulosclerosis, chronic and acute renal failure, a coronary heart disease, angina pectoris, myocardial infarction, apoplexy, restenosis, endothelial dysfunction, degraded blood vessel compliance, congestive heart failure and the like can be mentioned. Particularly, the mild, moderate and severe "hypertension" defined in J. Hypertension 1999, 17, 151-183, particularly page 162, is preferably treated, where particularly preferentially treated is "isolated systolic hypertension" (ISH).

In addition to the above, "diabetes or disorder thereof" such as hyperglycemia, hyperinsulinemia, diabetes, an insulin resistant glucose metabolism disorder, an IGT condition, an impaired fasting plasma glucose condition, obesity, diabetic retinopathy, diabetic nephropathy, glomerulosclerosis, diabetic neuropathy, metabolic syndrome and the like, and "hyperlipidemia or disorder thereof" such as hyperlipidemia, hypertriglyceridemia, a coronary heart disease, restenosis, endothelial dysfunction, obesity, degraded blood vessel compliance and the like can be mentioned.

In the concomitant drug of the present invention, a salt of compound 2 with organic or inorganic, mono- or di-basic acid or a solvate thereof, and an other active ingredient of a pharmaceutical agent selected from antidiabetic drug, HMG-CoA reductase inhibitor and antihypertensive drug, a pharmaceutically acceptable salt thereof or a solvate thereof are administered in combination, whereby a beneficial, particularly, enhancing or synergistic therapeutic effect can be obtained for the above-mentioned disease and the like.

A further advantage of the concomitant drug of the present invention is possible reduction of dose by using a low dose of individual pharmaceutical agents to be combined. For example, the advantage includes not only the low dose but also less application frequency, less development of side effects and the like. Note that the advantage is subject to change depending on the wish of the patients to be treated, necessary conditions and the like.

The concomitant drug of the present invention is used for oral administration to warm-blooded mammals, and can contain the above-mentioned pharmacologically active compound alone or together with carrier for preparations and the like.

For example, the concomitant drug of the present invention contains the active compound in a proportion of about 0.1%-about 90%, preferably about 1%-about 80%. This can be produced by a method known per se, for example, by conventional mixing, granulation, coating, solubilizing or freeze-drying steps.

For example, an oral pharmaceutical composition can be obtained by mixing the active compound with a solid excipient, granulating, where desired, the obtained mixture, adding an appropriate auxiliary substance as necessary, and processing the mixture or granule into tablet or sugar-coated tablet core and the like.

While the dose of the concomitant drug of the present invention to be administered to a target warm-blooded mammal varies depending on various factors, for example, administration method, and the species, age and/or individual condition of the warm-blooded mammal, those of ordinary skill in the art can appropriately determined the dose. Preferable dose of the active ingredient of the concomitant drug of the present invention is a therapeutically effective amount, particularly a commercially available dose.

Conventionally, for oral administration of the concomitant drug of the present invention, a general daily dose for a patient with body weight of 75 kg is, for example, about 1 mg-about 360 mg, preferably about 1 mg-about 100 mg, more preferably about 1 mg-about 50 mg, of a salt of compound 2 with mono- or di-basic acid or a solvate thereof, and other pharmaceutical agent can be administered simultaneously or at any intervals.

Specific examples of a combination of a salt of compound 2 with organic or inorganic, mono- or di-basic acid or a solvate thereof and a representative other pharmaceutical agent are shown below.

For a combination with an insulin secretagogue, the insulin secretagogue is administered at a dose range of about 0.01 mg-about 8 mg, preferably about 0.5-about 6 mg.

For a combination with an HMG-CoA reductase inhibitor, its preferable dose unit form is, for example, a tablet or capsule containing an HMG-CoA reductase inhibitor in about 5 mg-about 120 mg. Preferably, when fluvastatin is used, for example, a combination containing 20 mg, 40 mg or 80 mg (corresponding to free acid) of fluvastatin is administered, for example, once a day.

For a combination with an ACE inhibitor, its preferable dose unit form includes, for example, a tablet or capsule containing benazepril in about 5 mg-about 20 mg, preferably 5 mg, 10 mg, 20 mg, more preferably 40 mg, a tablet or capsule containing captopril in about 6.5 mg-about 100 mg, preferably 6.25 mg, 12.5 mg, 25 mg, 50 mg, 75 mg or 100 mg, a tablet or capsule containing enalapril in about 2.5 mg-about 20 mg, preferably 2.5 mg, 5 mg, 10 mg or 20 mg, a tablet or capsule containing fosinopril in about 10 mg-about 20 mg, preferably 10 mg or 20 mg, a tablet or capsule containing perindopril in about 2.5 mg-about 4 mg, preferably 2 mg or 4 mg, a tablet or capsule containing quinapril in about 5 mg-about 20 mg, preferably 5 mg, 10 mg or 20 mg, and a tablet or capsule containing ramipril in about 1.25 mg-about 5 mg, preferably 1.25 mg, 2.5 mg or 5 mg.

For a combination with valsartan, which is a representative AT1 receptor antagonist, the agent is supplied in an appropriate dose unit form (for example, capsule or tablet) containing a therapeutically effective amount of valsartan administrable to patients (for example, about 20 mg-about 320 mg, preferably about 80 mg-about 320 mg).

While the present invention has been explained taking a concomitant drug for example in the above, the above-mentioned explanation directly applies to the prophylactic and/or therapeutic method of the present invention.

EXAMPLES

The present invention is explained in detail in the following by referring to Examples, which are not to be construed as limitative. In the following Examples, compound 2 synthesized according to the production method described as Example 222 of WO02/14271 was processed to give 2.5 hydrobromide hydrate by a conventional method and used as "compound 3".

In the experiment, Basen tablet (Takeda Pharmaceutical Co., Ltd.) was used as Voglibose and metformin purchased from Sigma-Aldrich Corporation was used.

Experimental Example 1

Effect of Compound 3, Voglibose (α-glucosidase Inhibitor) and Combination Thereof on Plasma Glucose Level and Insulin Concentration in Oral Carbohydrate Loading Test of Zucker Fatty (Hereinafter to be Indicated as ZF) Rats (Test Method)

Figure 2:
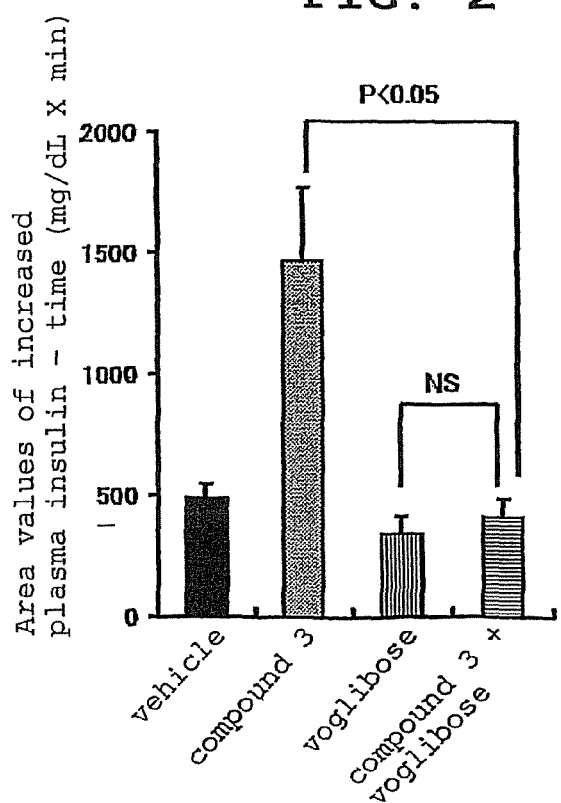
FIG. 2 The Figure shows the effect of compound 3 and voglibose on area values of increased plasma glucose concentration-time after oral carbohydrate loading, as well as the effect of a combination of compound 3 and voglibose in ZF rat. Each column shows mean±standard error. The time area value was calculated from the changes in the plasma insulin level for 60 min after carbohydrate loading. *$P<0.05$: comparison between compound 3 or voglibose alone (group 2 or 3) and combined use (group 4) (Student's t-test).

For this test, overnight fasted male ZF rats were used. Four groups each containing 5 rats were formed. Administration substances shown in the following Table were administered to the animals of each group. That is, 0.5% hydroxypropylmethylcellulose solution, which was the vehicle used for the preparation of compound 3 and voglibose, was given to group 1, compound 3 (0.1 mg/kg) was given to group 2, voglibose (0.1 mg/kg) was given to group 3, and a combination of compound 3 (0.1 mg/kg) and voglibose (0.1 mg/kg) was given to group 4. The dose was 2 mL/kg in all cases. After 15 min, a mixed carbohydrates solution of starch, sucrose and lactose (mixing rate 6:3:1) was orally administered at 3.5 g/kg. The dose of the carbohydrates solution was 10 mL/kg. Blood samples were collected over time, and plasma glucose concentration and insulin concentration were measured. The measurement results are respectively shown in FIGS. 1 and 2.

TABLE 1

| group | administration substance | dose | number of cases |
|---|---|---|---|
| 1 | 0.5% hydroxypropylmethylcellulose (vehicle) | 2 mL/kg | 5 |

TABLE 1-continued

| group | administration substance | dose | number of cases |
|---|---|---|---|
| 2 | compound 3 | 0.1 mg/kg | 5 |
| 3 | voglibose | 0.1 mg/kg | 5 |
| 4 | compound 3 voglibose | 0.1 mg/kg 0.1 mg/kg | 5 |

(Results)

In ZF rats, compound 3 and voglibose suppressed an increase in the plasma glucose after oral carbohydrate loading by 33% and 34%, respectively, as compared to the vehicle group. When compound 3 and voglibose were used in combination, the suppressive effect on increasing plasma glucose was more potent, leading to 71% of suppression, showing a significant difference from single use of each pharmaceutical agent. In addition, when compound 3 was used alone, the plasma insulin concentration increased about 3-fold as compared to the vehicle group. However, when combined with voglibose, the total insulin secretion effect was attenuated. The result indicates that compound 3 combined with voglibose enables control of plasma glucose with the smaller insulin secretion amount.

Experimental Example 2

Effect of Combination of Compound 3 and Metformin in Oral Carbohydrate Loading Test of ZF Rats (Test Method)

Figure 3:
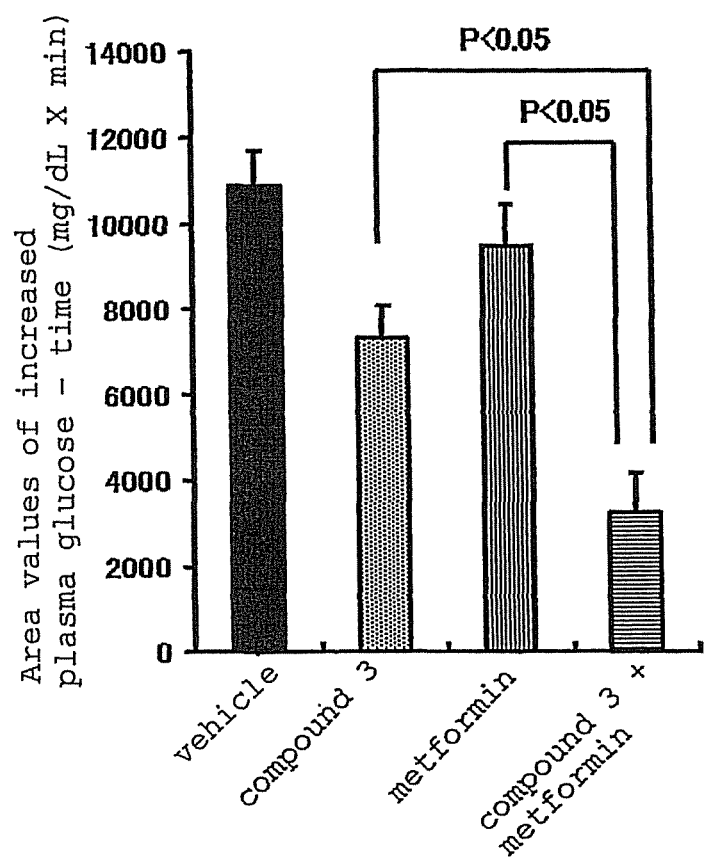
FIG. 3 The Figure shows the effect of compound 3 and metformin on area values of increased plasma glucose concentration-time after oral carbohydrate loading, as well as the effect of a combination of compound 3 and metformin in ZF rat. Each column shows mean±standard error. The time area value was calculated from the changes in the plasma glucose level for 120 min after carbohydrate loading. *$P<0.05$: comparison between compound 3 or metformin alone (group 2 or 3) and combined use (group 4) (Student's t-test).

For this test, overnight fasted male ZF rats were used. Four groups each containing 8 rats were formed. Administration substances shown in the following Table were administered to the animals of each group. That is, 0.5% hydroxypropylmethylcellulose solution, which was the vehicle used for the preparation of compound 3 and voglibose, was given to group 1, compound 3 (0.3 mg/kg) was given to group 2, metformin (50 mg/kg) was given to group 3, and a combination of compound 3 (0.3 mg/kg) and metformin (50 mg/kg) was given to group 4. The dose was 2 mL/kg in all cases. After 15 min, a mixed carbohydrates solution of starch, sucrose and lactose (mixing rate 6:3:1) was orally administered at 3.5 g/kg. The dose of the carbohydrates solution was 10 mL/kg. Blood samples were collected over time, and plasma glucose concentration was measured. The measurement results are shown in FIG. 3.

TABLE 2

| group | administration substance | dose | number of cases |
|---|---|---|---|
| 1 | 0.5% hydroxypropylmethylcellulose (vehicle) | 2 mL/kg | 8 |
| 2 | compound 3 | 0.3 mg/kg | 8 |
| 3 | metformin | 50 mg/kg | 8 |
| 4 | compound 3 metformin | 0.3 mg/kg 50 mg/kg | 8 |

(Results)

In ZF rats, compound 3 and metformin suppressed an increase in the plasma glucose after oral carbohydrate loading by 33% and 13%, respectively, as compared to the vehicle group. When compound 3 and metformin were used in combination, the suppressive effect on increasing plasma glucose was more potent, leading to 70% of suppression, showing a significant difference from single use of each pharmaceutical agent.

INDUSTRIAL APPLICABILITY

The concomitant drug of the present invention is effective as a therapeutic and/or prophylactic drug for type 2 diabetes, diabetic complications and the like, and promotes development as a pharmaceutical product.

This application is based on application No. 2005-164213 filed in Japan, the contents of which are incorporated hereinto by reference.

The invention claimed is:

1. A method for treating hyperglycemia, diabetes, an insulin resistant glucose metabolism disorder, an impaired glucose tolerance condition, or an impaired fasting plasma glucose condition in a warm-blooded mammal, which comprises simultaneously or separately administering
   (a) 1-50 mg of 3-{(2S,4S)-4-[4-(3-methyl-1-phenyl-1H-pyrazol-5-yl)piperazin-1-yl]pyrrolidin-2-ylcarbonyl}thiazolidine 2.5 hydrobromide, or a hydrate thereof, and
   (b) an antidiabetic drug selected from the group consisting of (i) a sulfonylurea agent, (ii) a glitazone, (iii) a biguanide, and (iv) an alpha-glucosidase inhibitor, or a pharmaceutically acceptable salt thereof,
to a warm-blooded mammal, thereby treating hyperglycemia, diabetes, an insulin resistant glucose metabolism disorder, an impaired glucose tolerance condition, or an impaired fasting plasma glucose condition in the warm-blooded mammal.

2. The method of claim 1, wherein the antidiabetic drug is at least one agent selected from the group consisting of metformin and an α-glucosidase inhibitor, and pharmaceutically acceptable salts thereof.

3. The method of claim 1, wherein the antidiabetic drug is selected from the group consisting of glimepiride, glipizide, and glyburide, or a pharmaceutically acceptable salt thereof.

4. The method of claim 1, wherein the antidiabetic drug is selected from the group consisting of pioglitazone, troglitazone, and rosiglitazone, or a pharmaceutically acceptable salt thereof.

5. The method of claim 1, wherein the antidiabetic drug is metformin or a pharmaceutically acceptable salt thereof.

6. The method of claim 1, wherein the antidiabetic drug is selected from the group consisting of acarbose, voglibose, and miglitol, or a pharmaceutically acceptable salt thereof.

7. A method of decreasing plasma glucose level in a warm-blooded mammal without causing insulin secretion, which comprises simultaneously or separately administering
   (a) 1-50 mg of 3-{(2S,4S)-4-[4-(3-methyl-1-phenyl-1H-pyrazol-5-yl)piperazin-1-yl]pyrrolidin-2-ylcarbonyl}thiazolidine 2.5 hydrobromide, or a hydrate thereof, and
   (b) an alpha-glucosidase inhibitor or a pharmaceutically acceptable salt thereof, to a warm-blooded mammal, thereby decreasing the plasma glucose level in the warm-blooded mammal.

* * * * *